US 6,662,668 B2

(12) United States Patent
Berkenbosch et al.

(10) Patent No.: US 6,662,668 B2
(45) Date of Patent: Dec. 16, 2003

(54) FLUID FLOW RATE SELECTOR

(75) Inventors: Lyle Berkenbosch, Bettendorf, IA (US); Sammy K. Mickelson, Bettendorf, IA (US)

(73) Assignee: Litton Systems, Inc., Woodland Hills, CA (US)

( * ) Notice: Subject to any disclaimer, the term of this patent is extended or adjusted under 35 U.S.C. 154(b) by 120 days.

(21) Appl. No.: 09/962,100

(22) Filed: Sep. 26, 2001

(65) Prior Publication Data

US 2003/0056601 A1 Mar. 27, 2003

(51) Int. Cl.$^7$ ................................................. G01F 1/00
(52) U.S. Cl. .......................................................... 73/861
(58) Field of Search ............................. 73/861; 251/208, 251/206, 207; 137/549

(56) References Cited

U.S. PATENT DOCUMENTS

| | | | | |
|---|---|---|---|---|
| 3,949,966 A | * | 4/1976 | Fabish | 251/206 |
| 4,037,623 A | * | 7/1977 | Beswick | 137/601.19 |
| 4,328,832 A | * | 5/1982 | Inada et al. | 137/625.4 |
| 4,546,921 A | * | 10/1985 | McCormack | 137/625.43 |
| 4,572,477 A | * | 2/1986 | Phlipot et al. | 251/285 |
| 4,723,567 A | * | 2/1988 | Phlipot et al. | 137/315.17 |
| 5,014,750 A | | 5/1991 | Winchell et al. | |
| 5,107,886 A | * | 4/1992 | Taylor | 137/501 |
| 6,095,491 A | | 8/2000 | Kriesel | |

FOREIGN PATENT DOCUMENTS

| | | |
|---|---|---|
| CA | 2 110 322 | 5/1995 |
| JP | 2001007120 | 11/2002 |

OTHER PUBLICATIONS

"Drip–Feed Apparatus with Flow Rate Selector and Air Embollism Prevention System", Kenneth Mason, Research Disclosure, No. 322, Feb. 1, 1991, p. 105.

* cited by examiner

Primary Examiner—Harshad Patel
(74) Attorney, Agent, or Firm—Lowe Hauptman Gilman & Berner, LLP

(57) ABSTRACT

The present invention is directed to a flow rate selector having a high flow position and a low flow position. The flow rate selector has a flow selector knob having a web. The web has a flat surface. At least two seals are mounted on the flat surface of the web. A retaining piece has two orifices of differing cross-sectional areas. The flow selector knob is rotatable relative to the retaining piece such that at least one seal can be aligned with either of the orifices to prevent fluid flow there through while allowing fluid flow through the other orifice. Cover 656 has conical outside diameter that seals against chamber in 654. This protects chamber 720 from foreign particles.

28 Claims, 8 Drawing Sheets

FLUID FLOW RATE SELECTOR

FIELD OF THE INVENTION

The present invention relates generally to fluid flow rate selectors, and more particularly, to a fluid flow rate selector using internal seals located on a flat surface instead of on a cylindrical surface to form an axial flow path.

BACKGROUND OF THE INVENTION

A fluid flow rate selector is used to select a fluid flow rate. A conventional fluid flow rate selector is marketed by Ottico Meccanica Italiana SpA under part number VP256 as depicted in FIG. 1 as reference number 100.

As depicted in FIG. 1, a flow rate selector knob 110 is rotated to select either a low or a high flow rate. The flow rate selector 100 has a fluid inlet 105 which can be attached to a source of pressure (not shown) using an NPT (National Pipe Thread) fitting (not shown). An outlet having a bayonet fitting 120 is connectable to a bayonet coupling 200. As explained below, when the bayonet coupling 200 is fully mated to the bayonet fitting 120, and the inlet is connected to the source of pressure, fluid or gas will flow through the fluid flow rate selector at the flow rate at the selected flow rate. The fluid flow rate selector 100 has a stationary cylindrical body 150 and the knob 110 is rotated relative thereto to select the desired flow rate. A cover 130 is pivoted relative to the knob 110 to expose the bayonet fitting 120.

As depicted in FIG. 2, the bayonet coupling 200 has a central fitting portion 205 having a pair of ramps 210 for engagement with the bayonet fitting 120 and a forwardly extending portion 220. A hose 230 connects the central fitting portion 205 to a user.

Refer now to FIG. 3 which is a cross-sectional view of the fluid rate flow selector 100 of FIG. 1. Positioned within the cylindrical body 150 is a poppet assembly portion 305, connected to the bayonet fitting 120 opposite the inlet 105. The central poppet assembly 305 is biased in a direction towards the bayonet fitting 120. The flow rate selector knob 110 includes a spring loaded ball assembly 320 which is biased radially inwardly to form a seal as explained below. The poppet body assembly 305 includes two or more orifices which extend radially outwardly from a chamber within which the poppet assembly 305 is located. The ball assembly 320 is brought into an engagement with an O-ring 340 which is mounted on an outer cylindrical surface of the poppet body assembly 305. As depicted in FIGS. 1 and 3, the fluid flow rate selector 100 has a high and a low flow rate. Thus, the flow rate selector knob 110 can be rotated to one of two positions in which the orifice 330 is not sealed and the other orifice 310 is sealed. The forwardly extending portion 220 of the bayonet coupling 200 is brought into engagement with the poppet 350 of the poppet assembly 305 causing the poppet to unseat so that fluid can flow around the poppet through the orifice and past the poppet 305.

Disadvantageously, in the fluid flow rate selector of FIGS. 1 and 3 flow rate selector, the sealing O-rings 340 are mounted on a cylindrical surface of the knob 110. The natural shape of the O-rings 340 is planer or flat and in order to be shaped or to conform to the outer cylindrical surface, have to be deformed. Because the O-rings 340 have to be deformed, and attempt to return to their original shape, the O-rings need to be fixed to the outer cylindrical surface using adhesive. Even using the adhesive, there are significant sealing problems associated with the prior art arrangement.

SUMMARY OF THE INVENTION

It is, therefore, an object of the present invention to provide a fluid flow rate configured such that moving internal seals are kept in their natural planar shape.

These and other objects of the present invention are provided by a fluid flow rate selector utilizing an inlet mounted on a retaining piece having at least two flow orifices of differing cross-sectional areas such that each flow orifice is capable of limiting fluid flow to a different rate. The flow orifices are formed in a flat planar surface of the retaining piece. On the retaining piece, a flow rate selector body is mounted such that it is free to rotate relative to the retaining piece. A set of seals is mounted on the flat surface of the rotatable flow rate selector body. The flow rate selector body is rotated to align the seals to block the flow orifices, thereby selecting a desired flow rate.

These and other objects of the present invention are achieved by a flow rate selector having a high flow position and a low flow position. The flow rate selector has a flow selector knob having a web. The web has a flat surface. At least two seals are mounted on the flat surface of the web. A retaining piece has two orifices of differing cross-sectional areas. The flow selector knob is rotatable relative to the retaining piece such that at least one seal can be aligned with either of the orifices to prevent fluid flow there through while allowing fluid flow through the other orifice.

The foregoing and other objects of the present invention are achieved by a flow rate selector having a high flow position and a low flow position. The flow rate selector has a flow selector knob having a web. The web has a flat surface. A seal is mounted on the flat surface of the web. A force balancing element is mounted on the flat surface of the web. A retaining piece has two orifices of differing cross-sectional areas. The flow selector knob is rotatable relative to the retaining piece such that the seal can be aligned with either of the orifices to prevent fluid flow there through while allowing fluid flow through the other orifice.

The foregoing and other objects of the present invention are achieved by a flow rate selector having a high flow position and a low flow position. The flow selector knob has a web. The web has a flat surface. A seal is mounted on the flat surface of the web. A force balancing element is mounted on the flat surface of the web. An outer shell has two orifices of differing cross-sectional areas located an equal distance from a center of the outer shell. The outer shell also has a cylindrical extension enclosing part of the flow selector knob. The flow selector knob is rotatable relative to the outer shell such that the seal can be aligned with either of the orifices to prevent fluid flow there through while allowing fluid flow through the other orifice.

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments and its several details are capable of modifications in various obvious respects, all without departing from the invention. Accordingly, the drawings and description thereof are to be regarded as illustrative in nature, and not as restrictive.

BRIEF DESCRIPTION OF THE DRAWINGS

The present invention is illustrated by way of example, and not by limitation, in the figures of the accompanying drawings, wherein elements having the same reference numeral designations represent like elements throughout, and wherein.

BEST MODE FOR CARRYING OUT THE INVENTION

Figure 4:
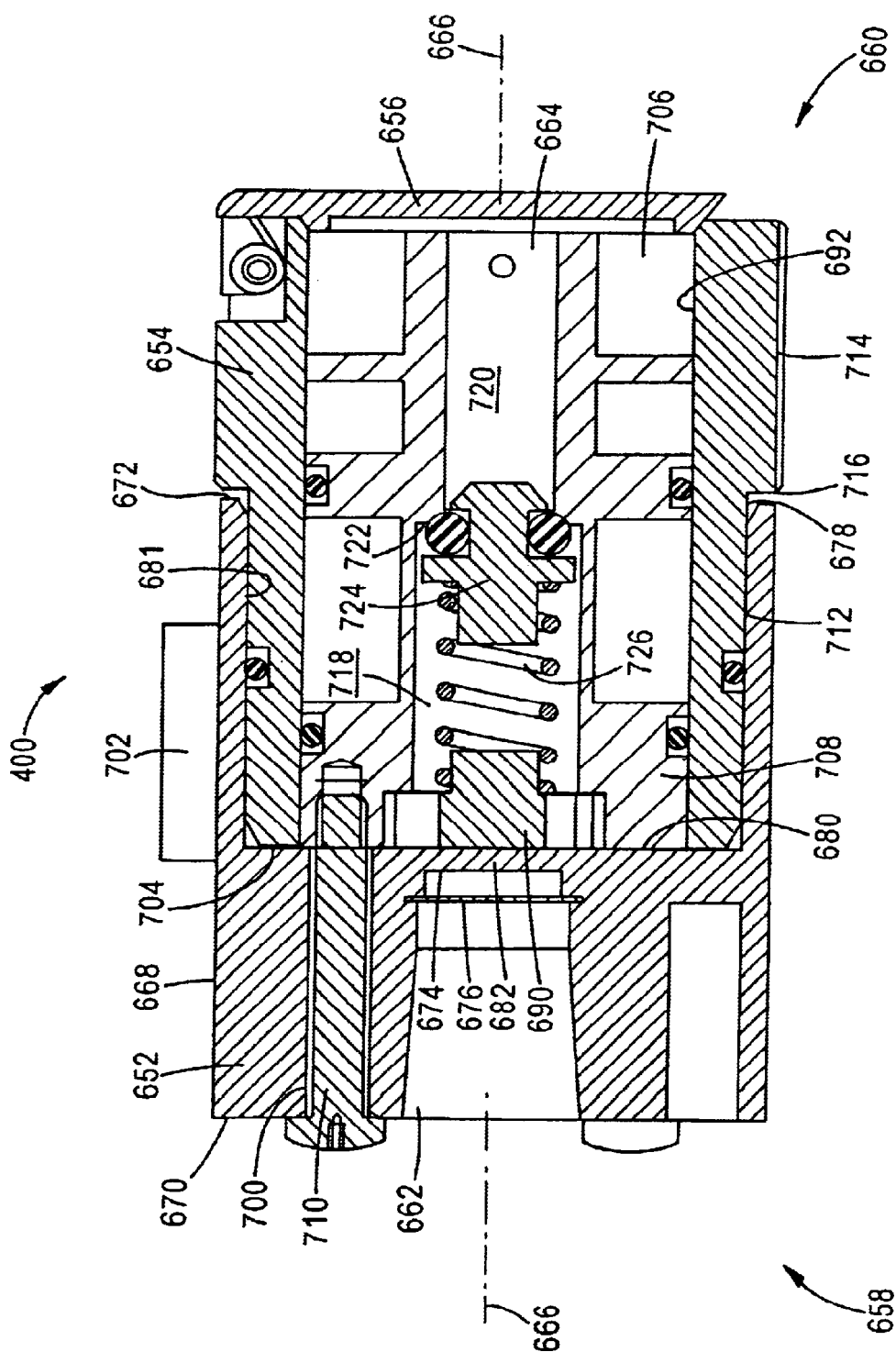
FIG. 4 is a cross-sectional view of the fluid flow rate selector according to the present invention.

Refer first to FIG. 4, where a flow rate selector assembly generally indicated at 400 according to the principles of the present invention is illustrated. Advantageously, as described herein, the flow rate selector 400, according to the present invention, provides an inline flow path with seals mounted on a rotatable flat surface with a stationary flat surface in sealing contact with the seals. The present invention reduces the number of parts compared to prior art devices that had seals mounted on cylindrical surfaces and provides excellent sealing because the seals are mounted in a natural condition and do not have to be deformed to fit on a cylindrical surface.

Figure 1:
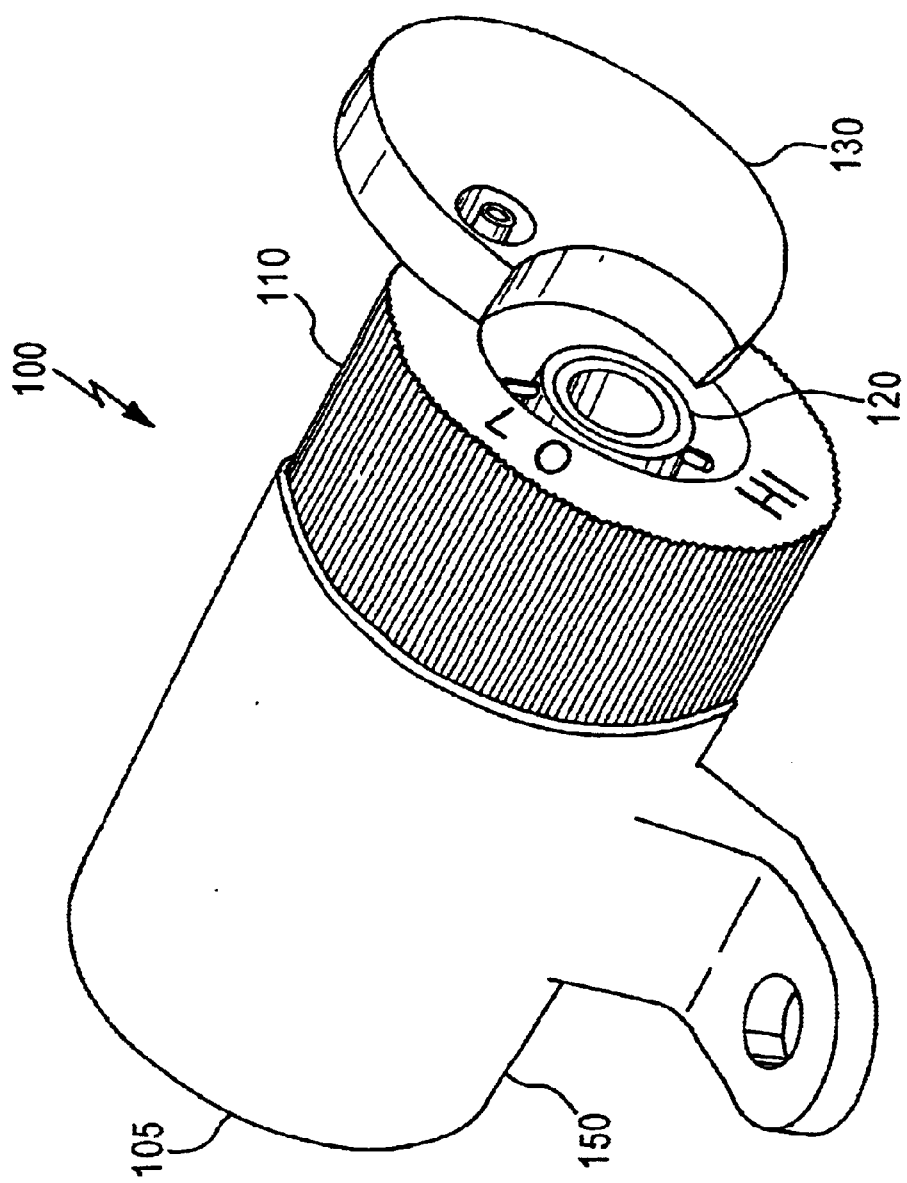
FIG. 1 is a perspective view of a prior art fluid flow rate selector.
Figure 2:
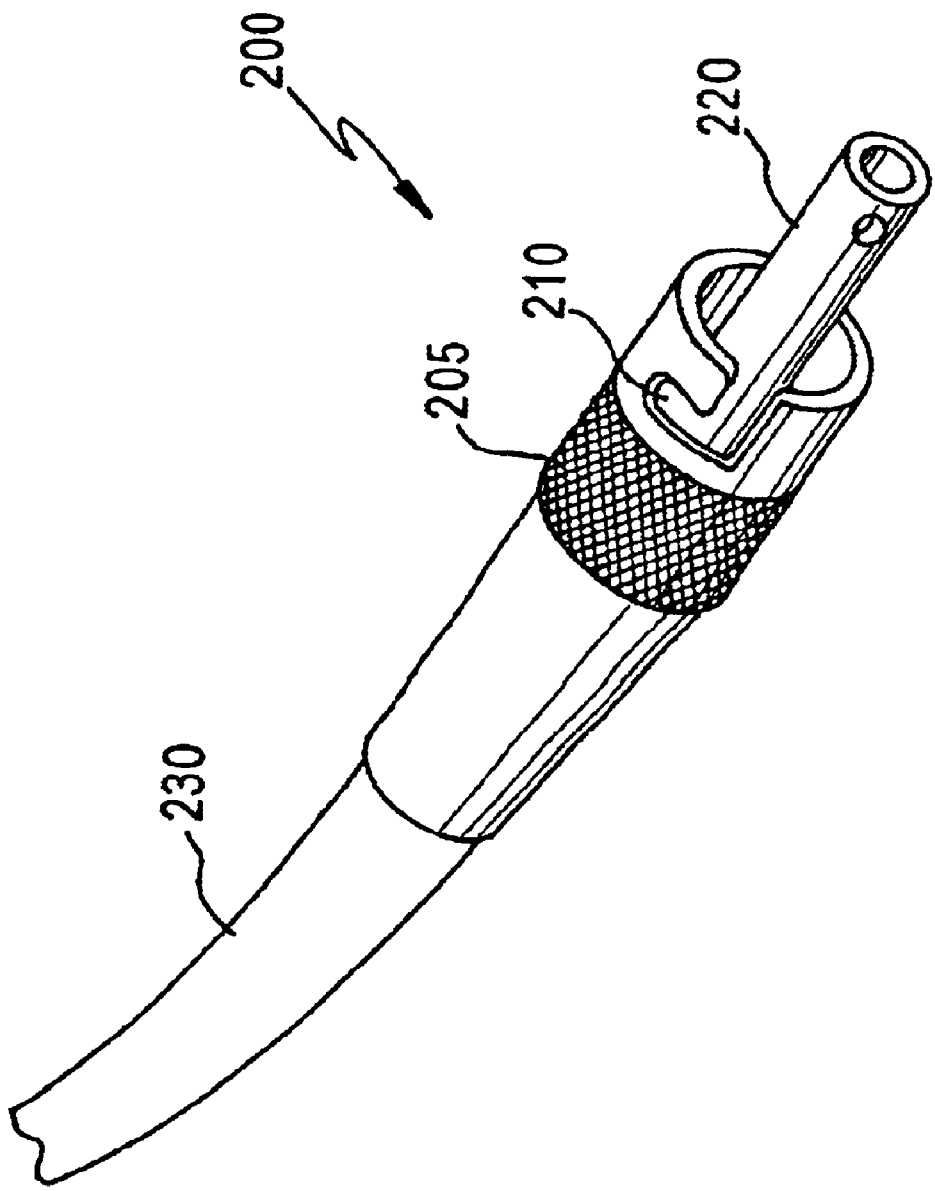
FIG. 2 is a perspective view of a prior art bayonet coupling usable with fluid flow rate selector depicted in FIG. 1.
Figure 3:
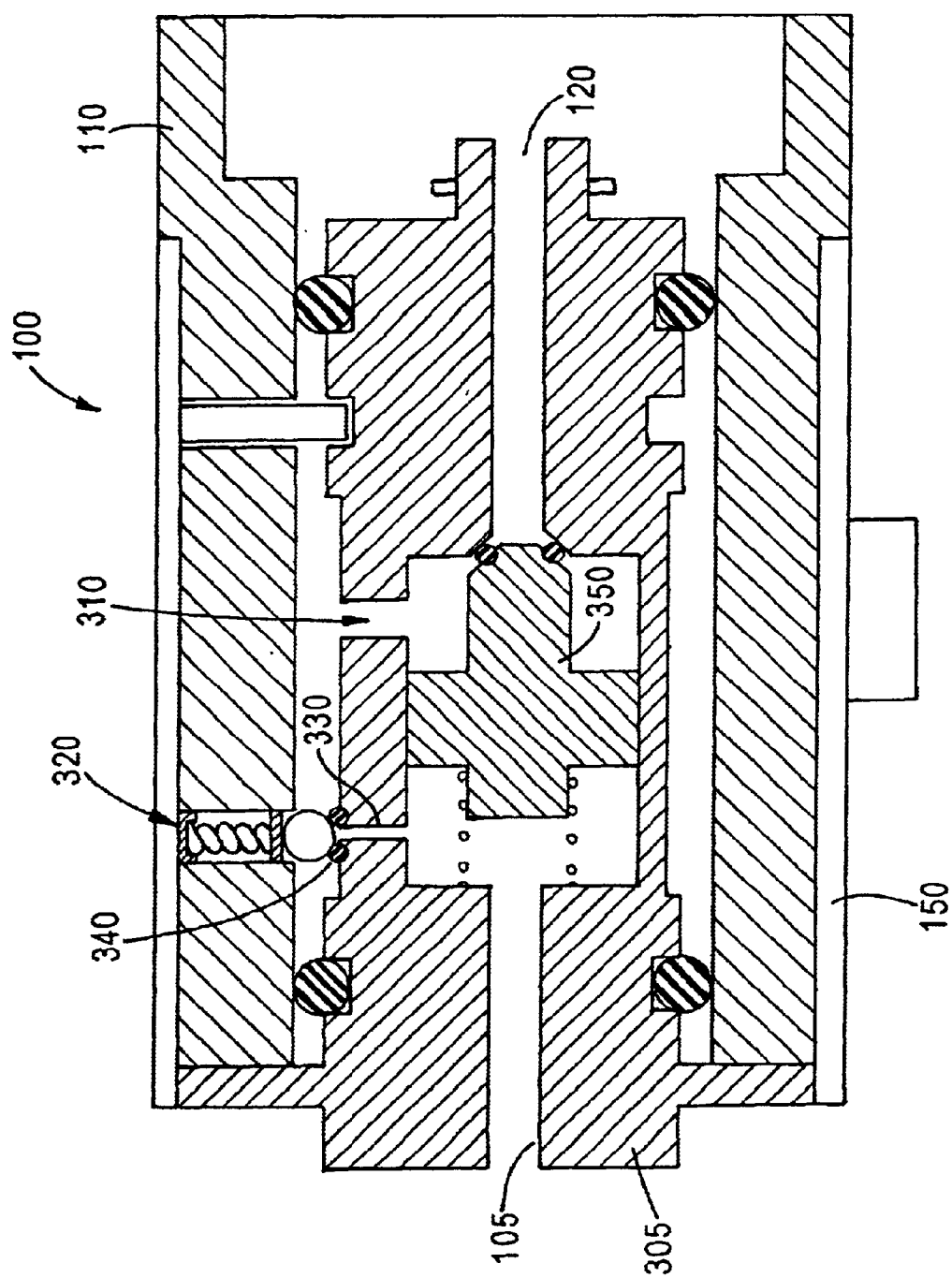
FIG. 3 is a cross-sectional view of a fluid flow rate selector of FIG. 1.

The fluid flow rate selector assembly 400 includes an outer shell 652, a generally cylindrical flow selector knob 654, and a protective end cap 656 fitted to the selector knob 654. The flow selector knob 654 is rotatable relative to the outer shell 652 and has a high flow position and a low flow position. According to the present invention, additional flow positions can be utilized. The fluid flow rate selector 400 has an inlet end 658 and an outlet end 660. The outer shell 652 has, at the inlet end 658, an inlet port 662 having female NPT threads connectable to a conduit attached to a fluid source with respect to FIG. 1. The end cap 656 has a closed position, depicted in FIG. 4, and an open position. When the end cap 656 is in the open position, an outlet port 664 recessed within the flow selector knob 654 is accessible and is connectable to a conduit with a bayonet mounting as previously described. The flow rate selector assembly 400 advantageously allows the user to connect a hose with MIL-DTL-7560/1 (bailout oxygen cylinder control assembly) fitting to the flow rate selector assembly 400 and then, by rotating the knob 654, select one of two flow levels. When the bayonet fitting 120 is not connected, a check valve (described below) prevents flow through the flow rate selector 400. The flow rate is set by routing the flow through one of two orifices in the outer shell 652. Flow through the non-selected orifice is stopped by rotating the knob 654, which surrounds the non-selected orifice with a seal, thereby blocking the flow path through that particular orifice. Meanwhile, fluid flows through the selected orifice at the selected flow rate.

The outer shell 652 has a generally cylindrical elongated shape with an external cylindrical surface 668 and two opposed circular end faces 670, 672 at the inlet end 658 and the outlet end 660, respectively. The inlet port 662, formed by a recess at the inlet end 658, has a flat bottom surface 674. Within the inlet port 662 is a filtering screen 676 oriented transverse to a longitudinal axis of the outer shell 652.

Another recess 678, with a diameter larger than that of the inlet port 662, extends inwardly from the end face 672 at the outlet end 660 to a flat bottom surface 680, which is spaced from the bottom surface 674 of the inlet port 662. A wall 682 is defined between the bottom surface 680 and the bottom surface 674. The recess 678 has a cylindrical surface 681 extending between the end face 672 and the bottom surface 680.

Figure 4A:
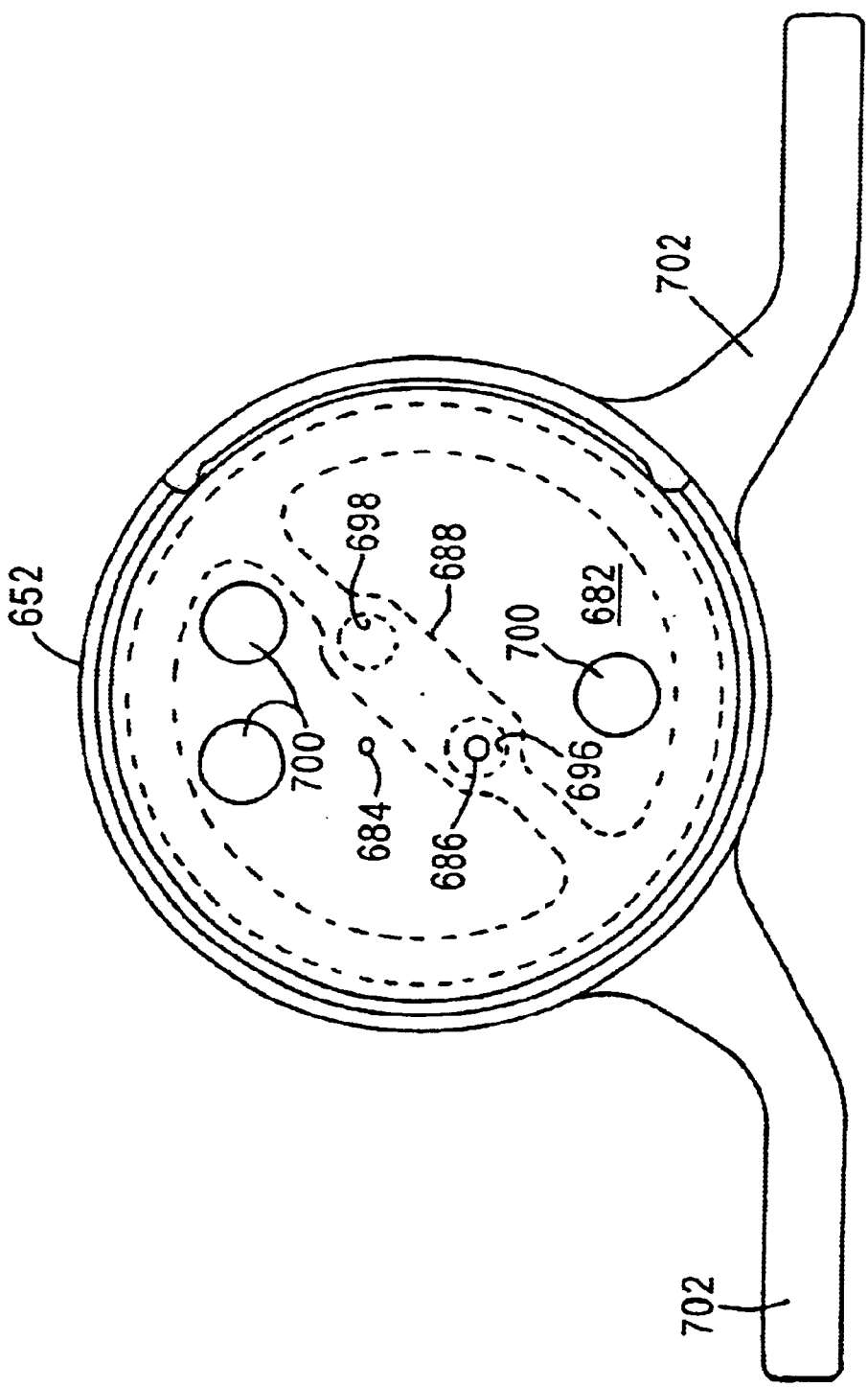
FIG. 4A is an end view depicting a web, seals and orifices in a first flow position.
Figure 4B:
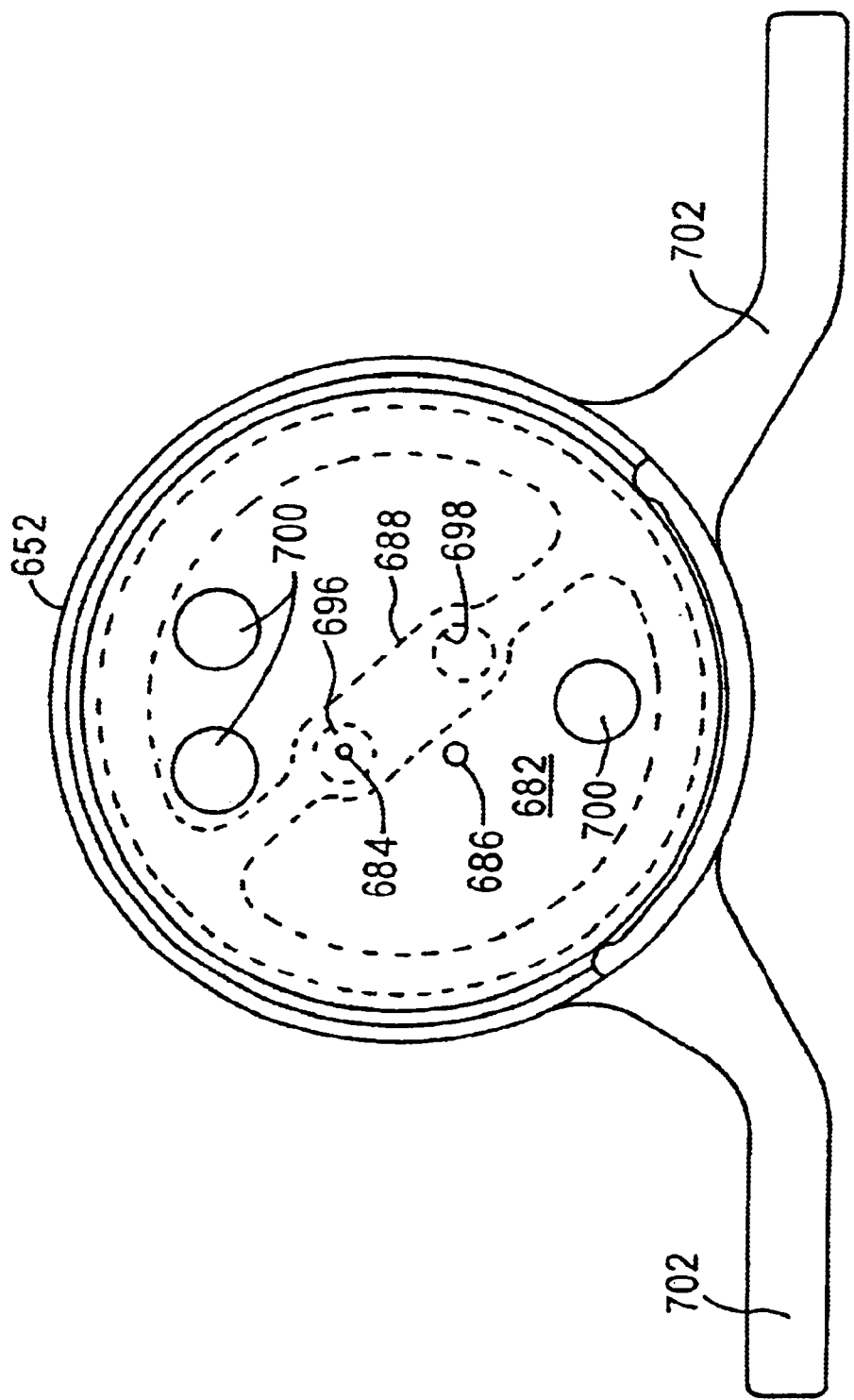
FIG. 4B is an end view, similar to FIG. 4A, depicting a second flow position.

Referring now to FIGS. 4A and 4B, an end view of the outer shell 652 from the outlet end 660 is illustrated indicating the positions of two orifices 684, 686 defined in the wall 682. Either of the orifices 684, 686 create a flow path between the inlet port 662 and the recess 678. Phantom markings 688 indicate the position of a web 690, explained in detail below, that is part of the flow selector knob 654.

As depicted in FIGS. 4, 4A and 4B the web 690 extends across a hollow central area of the knob 654 at one end thereof to be brought into contact with the bottom surface 680. The web 690 has a surface 694 at the inlet end 658 on which are attached two O-rings 696, 698. O-rings 696, 698 are circumferentially spaced on equal distance from a centerline of the flow selector 400 as are orifices 684, 686 such that in one position O-ring 696 covers orifice 686 and in another position O-ring 696 covers orifice 684.

The low and high flow positions of the flow selector knob 654 can now be explained. FIG. 4A illustrates the outer shell 652 with the phantom markings 688 depicting the web 690 in the low flow position. In the low flow position the O-ring 696 overlays the larger orifice 686 and blocks fluid flow there through. Fluid flows only through the smaller orifice 684. FIG. 4B illustrates the outer shell 652 with the phantom markings 688 indicating that the web 690 has been rotated in a clockwise direction into the high flow position; that is, the web 690 and an O-ring 696 overlay the smaller orifice 684 and block fluid flow there through. Fluid flows only through the larger orifice 686. Only one of the O-rings 696, 698 is used to seal an orifice 684, 686.

The other O-ring serves only to balance the force of the flow selector knob 654 against the wall 682. It should be understood that although the O-rings are preferred, other types of seals could be used.

Referring back to FIG. 4, the outer shell 652 also has three bolt holes 700 extending axially from the end face 670 at the inlet end 658 through the bottom surface 680. The bolt holes 700 must be located not to restrict travel of the flow selector knob 654. The outer shell 652 further has two legs 702 extending generally radially outwardly from the cylindrical surface 668 for enabling the selector 400 to be securely mounted to another surface using holes 640 (FIG. 6) formed in legs 702.

The flow selector knob 654 has a generally cylindrical shape with a circular end face 704 in contact with the bottom surface 680. The flow selector knob 654 has a portion of it mounted within the recess 678 of the outer shell 652. The flow selector knob 654 is hollow and has a circular through bore 706 into which a poppet body 708 is positioned. Bolts 710 extend through the bolt holes 700 and are connected to the poppet body 708 such that the poppet body 708 is fixed relative to the outer shell 652.

The flow selector knob 654 has a smaller diameter portion 712 at the inlet end 658 and a larger diameter portion 714 at the outlet end 660. A shoulder 716 is defined between the smaller diameter portion 712 and the larger diameter portion 714. The larger diameter portion 714 has a knurled or ridged surface to facilitate grasping by a user when desired to rotate the knob 654 to change flow rate.

The poppet body 708 has a first internal chamber 718 terminating approximately midway between the inlet end 658 and the outlet end 660. Also within the poppet body 708 is an outlet 720 extending from the outlet end 660 to the first internal chamber 718. The cross-sectional diameter of the first internal chamber 718 is less than the cross-sectional diameter of the outlet 720, so an internal shoulder 722 is formed where the chamber 718 and the outlet 720 coincide. A check valve is formed within the poppet body 708 by a poppet 724 biased against the internal shoulder 722 by a spring 726 connected to the poppet 724 at one end and to the web 690 at the other end.

Figure 5B:
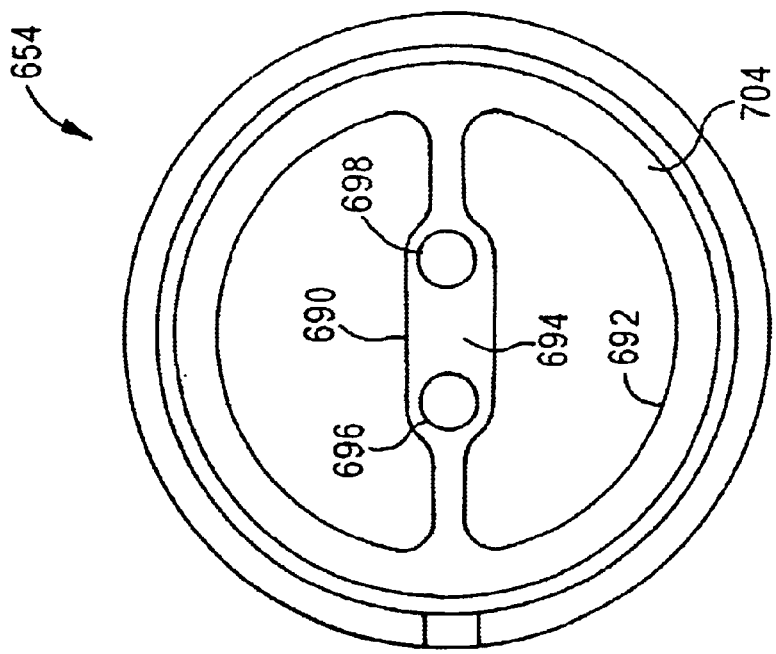
FIGS. 5A and 5B are side and end views of the fluid flow rate selector knob body, respectively.
Figure 5A:
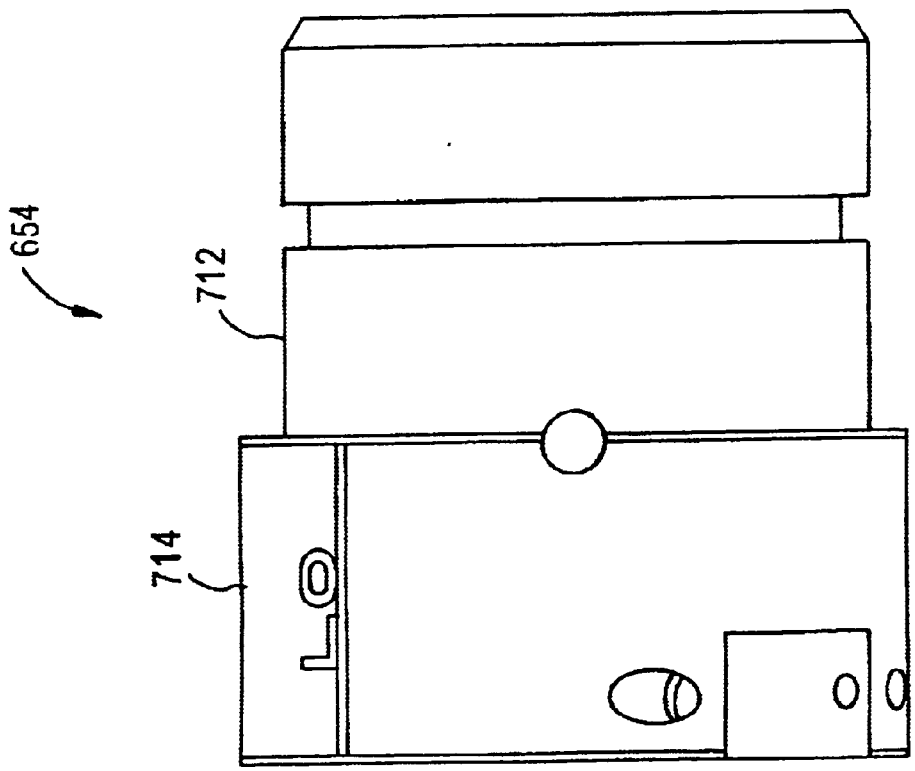

As depicted in FIG. 5B, the flow knob body 654 has a hollow central section bounded by a cylindrical wall 692 (FIG. 5A). The web extends across the hollow central section but only covers a small portion of the central hollow portion.

Figure 6:
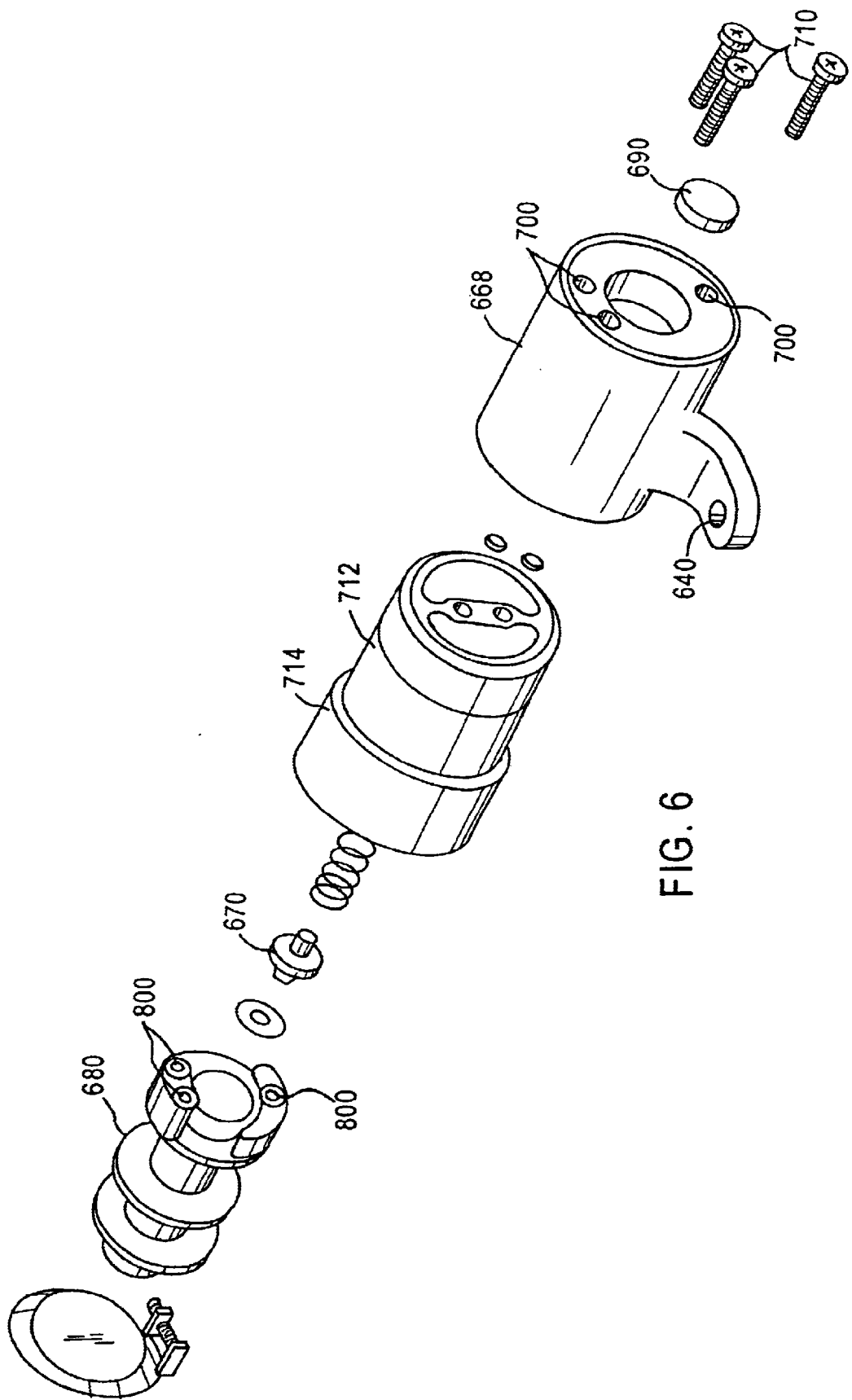
FIG. 6 is an exploded view of the fluid flow rate selector.

FIG. 6 is an exploded view of the flow rate selector 400 of FIG. 4. The poppet body portion is shown in greater detail where two stops 800 are provided for stopping relative rotation of the web.

The flow of fluid through the flow rate selector 400 will now be described. Fluid enters the flow rate selector 400 at the inlet port 662, passes through the filtering screen 676. Fluid then flows through either orifice 684 or 686, whichever is not blocked by the web 690 as explained above with reference to FIGS. 4A and 4B. Fluid exiting an unblocked orifice passes around the web 690 and into the chamber 718 within the poppet body 708. The poppet 724 biased against the internal shoulder 722 prevents further fluid flow. However, when connecting the outlet port 664 to a conduit with a bayonet mount as discussed above, the hollow protrusion of the bayonet mount contacts the poppet 724 and moves it rearwardly from the internal shoulder 722. Fluid then flows through the chamber 720 and out the outlet mount 664. The knob 654 can be rotated to the other position to change the flow rate.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof

What is claimed is:

1. A flow rate selector having a high flow position and a low flow position, said flow rate selector comprising:
   a flow selector knob having a web, said web having a flat surface;
   at least two seals mounted on said flat surface of said web; and
   a retaining piece having two orifices of differing cross-sectional areas;
   wherein said flow selector knob is rotatable relative to said retaining piece such that at least one seal can be aligned with either of said orifices to prevent fluid flow there through while allowing fluid flow through the other orifice.

2. The flow rate selector of claim 1, wherein said flow selector knob has a first end and a second end, and a cylindrical passage having a cylindrical surface extending from said first end to said second end, said web being on one end of said flow selector knob and extending diametrically across said cylindrical passage and attached at opposite ends to diametrically opposed portions of said cylindrical surface.

3. The flow rate selector of claim 2, wherein said web forms a first arc shaped opening and a second arc shaped opening.

4. The flow rate selector of claim 3, further comprising a poppet body positioned in said cylindrical passage.

5. The flow rate selector of claim 4, wherein said poppet body has an internal passage having an inlet and an outlet and further comprising a poppet which is biased into a closed position, said poppet being opened by connecting a bayonet connector to said flow rate selector.

6. The flow rate selector of claim 5, wherein said poppet body is connected to said retaining piece by one or more bolts extending through at least one of said first or second arc shaped openings.

7. The flow rate selector of claim 6, wherein the web abuts at least one bolt when the flow selector knob is in the high flow position or in the low flow position.

8. The flow rate selector knob of claim 6, wherein the web of said flow selector knob is positioned between said poppet body and said retaining piece to retain said flow selector knob in said flow rate selector.

9. The flow rate selector of claim 5, further comprising a coil spring expandable and contractible along an axial direction of said cylindrical passage, said coil spring having opposite longitudinal ends engaging said poppet and said web, respectively, for biasing said poppet and said web away from each other.

10. The flow rate selector of claim 4, further comprising:
    a poppet; and
    a spring;
    wherein said spring biases said web of said flow selector knob against said retaining piece while simultaneously biasing the poppet into said closed position.

11. The flow rate selector of claim 2, wherein each of said orifices, when not in alignment with said at least one seal, is in fluid communication with said cylindrical passage.

12. The flow rate selector of claim 1, wherein said two orifices are each an equal distance radially from a center of said retaining piece.

13. The flow rate selector of claim 12, wherein the angle formed by the two orifices with the center of said retaining piece as the vertex is less than 180 degrees.

14. The flow rate selector of claim 13, wherein the angle formed by the two orifices with the center of said retaining piece as the vertex is about 90 degrees.

15. The flow rate selector of claim 1, wherein the seals are mounted on said flat surface at equal distances radially from a center of said flat surface and on opposite sides of the center of said flat surface.

16. The flow rate selector of claim 1, wherein in said high flow position a first of said seals is aligned with one of said orifices to block fluid flow there through, in said low flow position the first of said seals is aligned with the other of said orifices to block fluid flow there through, and the second of said seals in both of said high flow position and said low flow position balances the force of said web against said retaining piece.

17. The flow rate selector of claim 1, wherein said retaining piece is a shell with a cylindrical extension enclosing part of the flow selector knob.

18. The flow rate selector of claim 1, wherein at least one said seals is an O-ring seal.

19. A flow rate selector having a high flow position and a low flow position, said flow rate selector comprising:
- a flow selector knob having a web, said web having a flat surface;
- a seal mounted on said flat surface of said web;
- a force balancing element mounted on said flat surface of said web; and
- a retaining piece having two orifices of differing cross-sectional areas;
- wherein said flow selector knob is rotatable relative to said retaining piece such that the seal can be aligned with either of the orifices to prevent fluid flow there through while allowing fluid flow through the other orifice.

20. The flow rate selector of claim 19, wherein the seal and the force balancing element are mounted on said flat surface at equal distances radially from a center of said flat surface and on opposite sides of the center.

21. The flow rate selector of claim 19, wherein in said high flow position the seal is aligned with one of said orifices to block fluid flow there through, and in said low flow position the seal is aligned with the other of said orifices to block fluid flow there through.

22. The flow rate selector of claim 19, wherein said web further has at least one through opening open to said flat surface, and each of said orifices, when not in alignment with said seal, is in fluid communication with said through opening.

23. A flow rate selector having a high flow position and a low flow position, said flow rate selector comprising:
- a flow selector knob having a web, said web having a flat surface;
- a seal mounted on said flat surface of said web;
- a force balancing element mounted on said flat surface of said web; and
- an outer shell having two orifices of differing cross-sectional areas located an equal distance from a center of the outer shell, said outer shell also having a cylindrical extension enclosing part of the flow selector knob;
- wherein said flow selector knob is rotatable relative to said outer shell such that the seal can be aligned with either of the orifices to prevent fluid flow there through while allowing fluid flow through the other orifice.

24. The flow rate selector of claim 23, wherein said flow selector knob has a first end and a second end, and a cylindrical passage having a cylindrical surface extending from said first end to said second end, said web being on one end of said flow selector knob and extending diametrically across said cylindrical passage and attached at opposite ends to diametrically opposed portions of said cylindrical surface, and wherein said web forms a first arc shaped opening and a second arc shaped opening.

25. The flow rate selector of claim 24, further comprising a poppet body positioned in said cylindrical passage and connected to said outer shell by one or more bolts extending through at least one of said first or second arc shaped openings, said poppet body having an internal passage with an inlet, an outlet, and a poppet which is biased into a closed position, said poppet being opened by connecting a bayonet connector to said flow rate selector.

26. The flow rate selector of claim 25, wherein the web abuts at least one bolt when the flow selector knob is in the high flow position or in the low flow position.

27. The flow rate selector knob of claim 25, wherein the web of said flow selector knob is positioned between said poppet body and said retaining piece to retain said flow selector knob in said flow rate selector.

28. The flow rate selector of claim 24, wherein each of said orifices, when not in alignment with said seal, is in fluid communication with said cylindrical passage.

* * * * *